(12) United States Patent
Hine et al.

(10) Patent No.: US 7,386,351 B2
(45) Date of Patent: Jun. 10, 2008

(54) METHOD AND APPARATUS FOR PLACING A CORONARY SINUS/CARDIAC VEIN PACING AND DEFIBRILIATION LEAD WITH ADJUSTABLE ELECTRODE SPACING

(75) Inventors: Douglas S. Hine, White Bear Lake, MN (US); John L. Sommer, Coon Rapids, MN (US); James H. Vaughan, Blaine, MN (US); Rick D. McVenes, Isanti, MN (US); Paulus C Van Venrooij, Hoensbroek (NL); Pierre-Andre Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 724 days.

(21) Appl. No.: 10/136,777

(22) Filed: Apr. 30, 2002

(65) Prior Publication Data

US 2003/0204231 A1    Oct. 30, 2003

(51) Int. Cl.
*A61N 1/05* (2006.01)
(52) U.S. Cl. .................................. 607/122
(58) Field of Classification Search ............ 600/373, 600/374, 377, 381; 607/116, 119, 122, 123, 607/126, 127, 130, 131
See application file for complete search history.

(56) References Cited

U.S. PATENT DOCUMENTS

| | | | |
|---|---|---|---|
| 4,458,677 A | 7/1984 | McCorkle, Jr. | |
| 4,798,206 A * | 1/1989 | Maddison et al. | 607/122 |
| 5,545,200 A * | 8/1996 | West et al. | 607/122 |
| 5,683,445 A * | 11/1997 | Swoyer | 607/125 |
| 5,755,766 A | 5/1998 | Chastain et al. | |
| 5,964,795 A * | 10/1999 | McVenes et al. | 607/122 |
| 5,991,668 A | 11/1999 | Leinders et al. | 607/125 |
| 6,070,104 A | 5/2000 | Hine et al. | 607/123 |
| 6,185,464 B1 * | 2/2001 | Bonner et al. | 607/119 |
| 6,192,280 B1 * | 2/2001 | Sommer et al. | 607/122 |
| 2001/0012958 A1 | 8/2001 | Audoglio | |

FOREIGN PATENT DOCUMENTS

| | | |
|---|---|---|
| EP | 0 965 359 | 12/1999 |
| WO | WO 03/009894 | 2/2003 |

\* cited by examiner

*Primary Examiner*—Carl Layno
*Assistant Examiner*—Frances P. Oropeza
(74) *Attorney, Agent, or Firm*—Michael C. Soldner; Carol F. Barry; Steve Bauer (57) ABSTRACT

A medical electrical lead, which may be useful in coupling an implantable medical device, is comprised of a first and second lead. The first lead has a first electrode coupled adjacent a distal end portion thereof. The distal end portion of the first lead is anchorable in the coronary sinus of a patient. The second lead is coupled with and moveable along the first lead. The second lead has a second electrode located thereon wherein the position of the first and second electrodes may be varied relative to one another by movement of the second lead along the first lead. A rubber tip holds the relative position of each electrode.

22 Claims, 8 Drawing Sheets

METHOD AND APPARATUS FOR PLACING A CORONARY SINUS/CARDIAC VEIN PACING AND DEFIBRILIATION LEAD WITH ADJUSTABLE ELECTRODE SPACING

BACKGROUND OF THE INVENTION

1. Field of the Invention

This invention relates generally to a method and apparatus for electrically stimulating a heart, and, more particularly, to a method and apparatus for positioning a multi-electrode lead to stimulate and/or sense activity in the heart.

2. Description of the Related Art

Since the introduction of the first implantable pacemakers in the 1960s, there have been considerable advancements in both the field of electronics and medicine, such that there is presently a wide assortment of commercially available body-implantable electronic medical devices. The class of implantable medical devices now includes therapeutic and diagnostic devices, such as pacemakers, cardioverters, defibrillators, neural stimulators, and drug administering devices, among others. Today's state-of-the-art implantable medical devices are vastly more sophisticated and complex than early ones, capable of performing significantly more complex tasks. The therapeutic benefits of such devices have been well proven.

Modem electrical therapeutic and diagnostic devices for the heart require a reliable electrical connection between the device and a region of the heart. Typically, a medical electrical "lead" is used for the desired electrical connection. One type of commonly used implantable lead is a transvenous lead. Transvenous leads are positioned through the venous system to attach or electrically connect at their distal end to the heart. At their proximal end, they are typically connected to the electrical therapeutic and diagnostic device, which may be implanted. Such leads normally take the form of a long, generally straight, flexible, insulated conductor. Among the many advantages of transvenous leads is that they permit an electrical contact with the heart without physically exposing the heart itself, i.e., major thoracic surgery is not required.

The specific design of transvenous leads is varied, depending upon the region of the heart to which it is to be connected. For example, U.S. Pat. No. 6,070,104 discloses an implantable lead capable of stimulating and/or sensing multiple chambers of the heart. Multiple electrodes are located on the lead and spaced apart so that multiple chambers may be separately stimulated and/or sensed. The structure and size of patients' hearts varies considerably. Accordingly, the optimal locations for positioning the electrodes within a vein may vary substantially, depending on the anatomy of the patient The spacing of the electrodes, however, is relatively fixed. Thus, optimally positioning the electrode associated with the ventricle of the heart may produce less than optimal positioning of the electrode associated with the atrium, or vice versa.

SUMMARY OF THE INVENTION

In one aspect of the present invention, a method is provided for positioning a medical electrical lead in a venous system and particularly in cardiac veins. The method includes inserting a first lead within the cardiac venous system wherein the first lead includes a first electrode. Thereafter, the first lead is anchored within the cardiac venous system, and an over-the-wire lead is guided into the cardiac venous system wherein the over-the-wire lead includes a second electrode and the first lead acts as a guide for the over-the-wire lead. The position of the second electrode relative to the first electrode may be adjusted by controlling the position of the over-the-wire lead relative to the first lead., In another aspect of the present invention, a medical electrical lead is provided. The medical electrical lead is comprised of a first and second lead. The first lead has a first electrode coupled adjacent a distal end portion thereof. The distal end portion of the first lead is anchorable in the coronary sinus of a patient. The second lead is coupled with and moveable along the first lead. The second lead has a second electrode located thereon wherein the position of the first and second electrodes may be varied relative to one another by movement of the second lead along the first lead.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Embodiments of the present invention concern a lead that may be implanted and used to stimulate, defibrillate, and/or sense the atrium and ventricle of the left side of the heart through a cardiac venous system, such as the coronary sinus and its tributaries. As is well known, there has to date been a great difficulty in reliably implanting leads within the coronary sinus. For example, a typical coronary sinus is 10 millimeters at its largest diameter (near the outflow to the right atrium) and narrows until it has a diameter of between approximately 2-3 millimeters and merges to the great cardiac vein. Thus any leads having larger sizes could be expected to diminish the flow of blood through the coronary sinus. The fixation of a lead within the coronary sinus is further complicated by the fact that, unlike a heart chamber where the fibrotic tissue response is used to assist lead fixation, no such fibrotic response can be expected in the vein. Thus, no fibrotic tissue response is available to assist in lead fixation. Moreover, variations among patients in the anatomy of the coronary sinus and the heart and therefore there is a need to accommodate these variations by allowing for adjustments in the spacing between the electrodes. Thus, one embodiment of the present invention includes a single lead with multiple electrodes whose position may be varied to stimulate, defibrillate, and/or sense the atrium and/or ventricle of the left side of the heart through the coronary sinus and its tributaries with a high degree of efficiency and accuracy.

Figure 1:
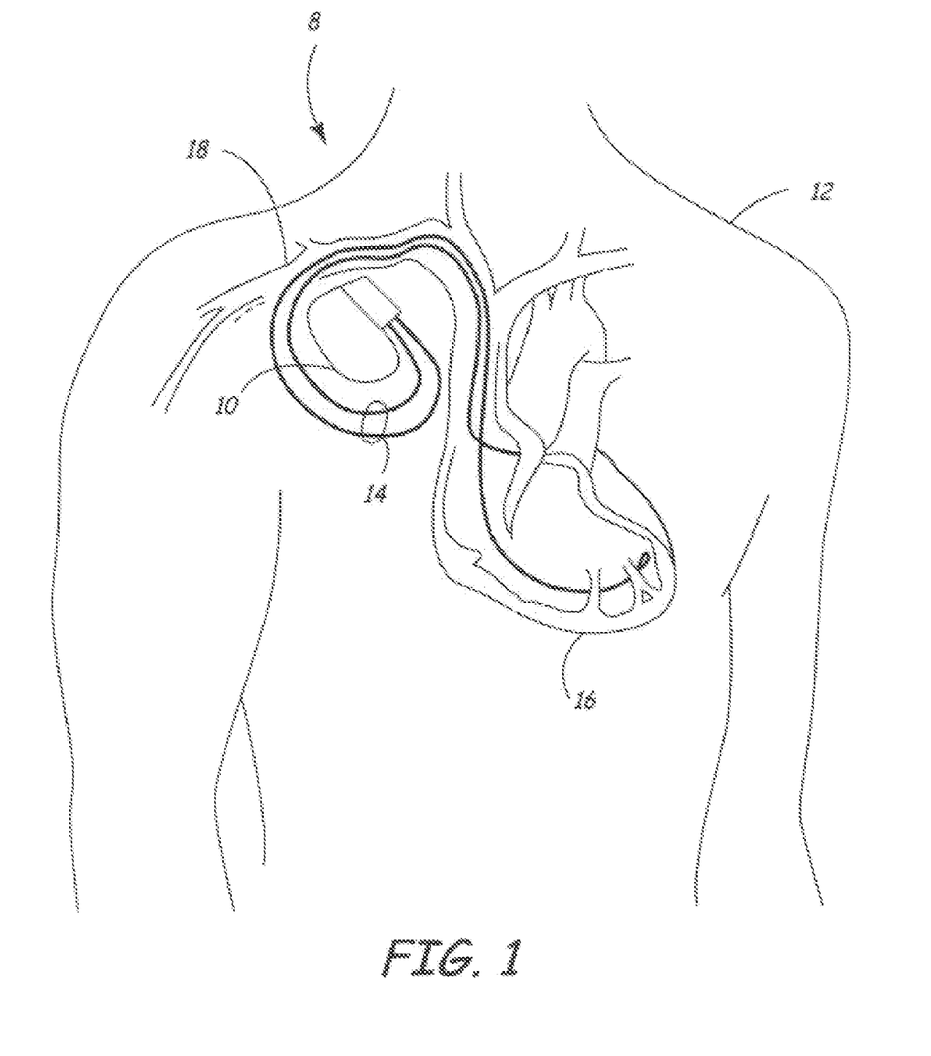
FIG. 1 schematically illustrates one embodiment of an implanted medical device in the form of a pacemaker and associated leads positioned to stimulate and/or sense the heart.

FIG. 1 illustrates an implantable medical device (IMD) system 8, which includes an implantable electronic device 10, such as a pacemaker, defibrillator, or the like, that has been implanted in a patient 12. The device 10 is housed within a hermetically sealed, biologically inert outer canister or housing, which may itself be conductive so as to serve as an electrode in the pacemaker's pacing/sensing circuit. One or more pacemaker leads, collectively identified with reference numeral 14 in FIG. 1 are electrically coupled to the pacemaker 10 in a conventional manner and extend into the patient's heart 16 via a vein 18. Disposed generally near a distal end of the leads 14 are one or more exposed conductive electrodes for sensing cardiac activity, delivering electrical pacing stimuli to the heart 16, or providing a stimulating voltage to defibrillate the heart 16. The leads 14 may be implanted with their distal end situated adjacent the atrium or the ventricle, or both, of the heart 16.

In the embodiments illustrated herein, some variations in the structure, construction, and/or location of the leads 14 may be useful in adapting the leads to their intended use. That is, the construction and/or positioning of the leads 14 may be altered when the leads 14 are used to variously provide left ventricle and atrial pacing, coronary sinus defibrillation, and/or left ventricle defibrillation. The process used to position the various embodiments at the various locations, however, is relatively similar. Accordingly, the process used for implanting and positioning the leads 14 will be discussed first herein. The method and apparatus useful in performing the various aspects of the implanting and positioning of the leads 14 are described in greater detail below in conjunction with FIGS. 2-4.

To the extent that certain components and procedures referenced herein are conventional in their design and operation, such components/procedures will not be described herein in detail, as it is believed that design and implementation of such components and the performance of such methods would be a matter of routine practice to those of ordinary skill in the art. For example, various processes for passing a catheter lead through the tortuous path of a representative cardiac venous system is well known in the art.

Figure 2A:
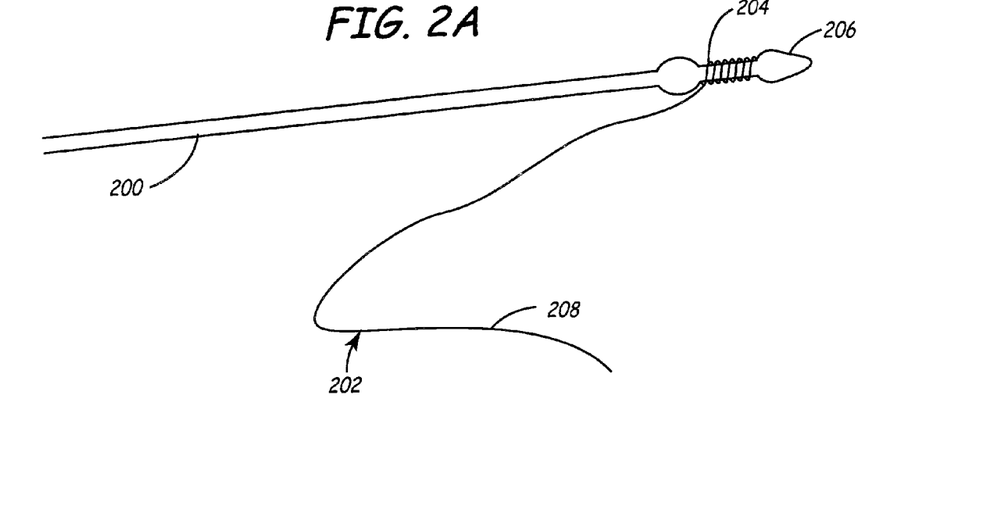
FIGS. 2A and 2B schematically illustrate a first and second embodiment of a balloon catheter that may be used to position the leads of FIG. 1.
Figure 3A:
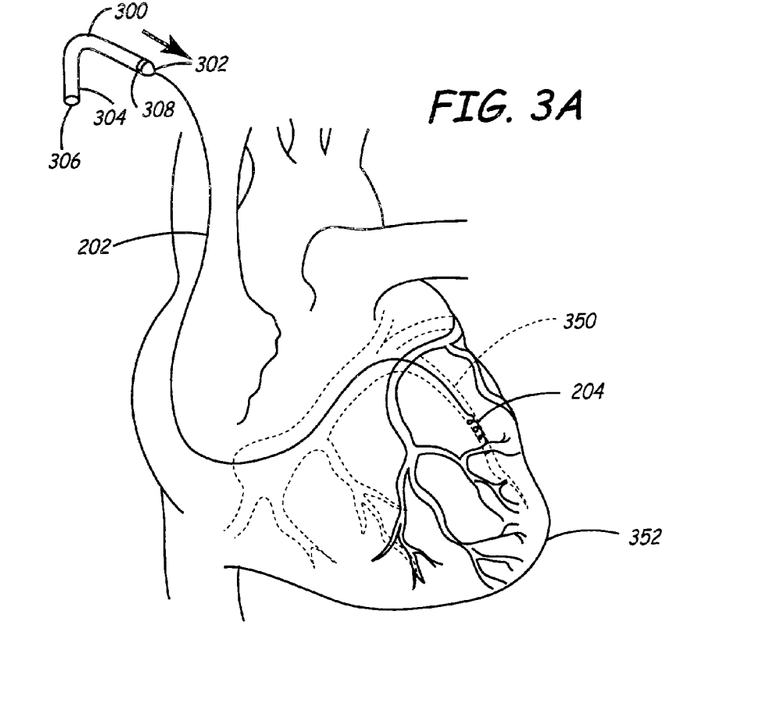
FIGS. 3A and 3B schematically illustrate a first and second embodiment of a first lead of FIG. 2 in its implanted position relative to a heart of a patient.

FIGS. 2A and 3A provide a stylized view of a first embodiment of a device, such as a balloon catheter 200, which may be used to pass a lead 202 through the cardiac venous system and then anchor a stent 204 in a desired location in a cardiac vein. Various well-known processes and apparatus for guiding the balloon catheter 200 through the cardiac venous system may be utilized to successfully locate and anchor the stent 204 and the lead 202, which in this embodiment takes the form of a fine wire 208. Accordingly, a detailed discussion of the apparatus and process will not be provided herein to avoid unnecessarily obscuring the instant invention.

Generally, in the illustrated embodiment the catheter 200 includes an inflatable balloon 206 adjacent its distal end portion. The stent 204 of the lead 202 may take on a variety of forms, but in the instant embodiment is generally a helical coil wound about the balloon 206. Thus, after the catheter 200 is guided through the cardiac venous system so that the stent 204 and the balloon 206 are at the desired location, the balloon 206 may be momentarily inflated, expanding the helical coil of the stent 204 into substantial contact with the interior walls of the vein. Thereafter, the balloon 206 may be deflated and the catheter 200 removed. At this point, as illustrated in FIG. 3A, the stent 204 is anchored in the vein 350 adjacent a chamber of the heart 352 that is to be sensed or stimulated. That is, the stent 204 is a first electrode that may be used to sense electrical activity associated with the chamber of the heart adjacent thereto and/or to deliver electrical stimulation to the adjacent chamber of the heart. Generally, a substantial portion of the stent 204 is in contact with a portion of the vein that is in contact with the heart. For example, the stent 204 is positioned to have more substantial contact with a first side of the vein adjacent the heart as opposed to a second side of the vein located opposite thereto, and thus more remote from the heart. This type of "directional" contact efficiently delivers stimulating signals to the heart, reduces the amount of the stimulating signal delivered to other portions of the body, less power is required to provide adequate stimulation, and sensing is more efficient.

Figure 4:
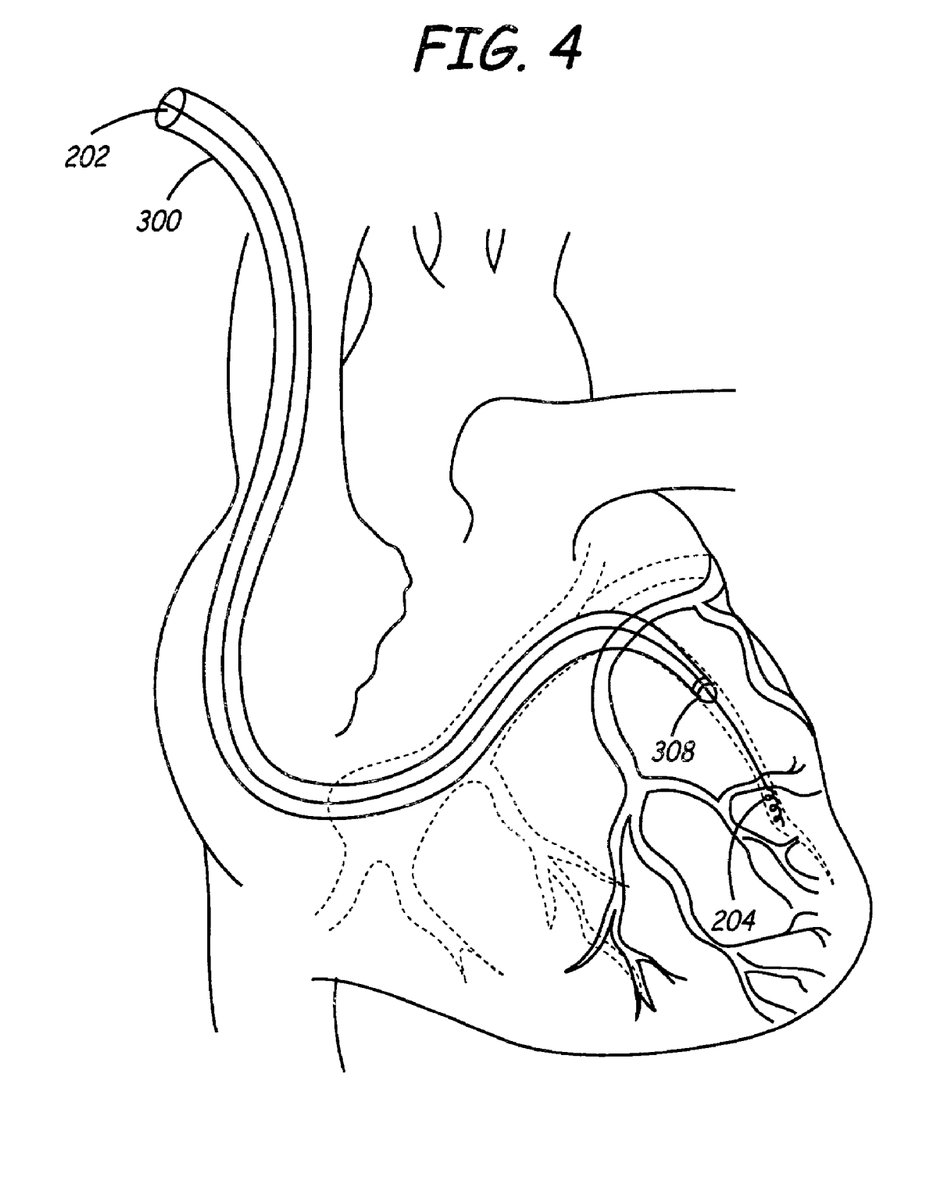
FIG. 4 schematically illustrates an over-the-wire lead positioned relative to the first lead of FIG. 3.

After the stent 204 is positioned, the lead 202 remains attached to the stent 204 via an insulated fine wire 208 and extends out through the cardiac venous system, remaining accessible to the surgeon performing the implantation. The lead 202 is next used as a guide for a second electrode, which in the instant embodiment takes the form of an over-the-wire lead 300. Generally, the over-the-wire (OTW) lead 300 includes a distal end 302, a proximal end 304, and a longitudinal passage 306 extending therebetween. An electrode 308 is positioned adjacent the distal end 302 of the OTW lead 300, and is ultimately intended to be located adjacent a chamber of the heart within the cardiac venous system to sense electrical activity associated with the chamber of the heart adjacent thereto and/or to deliver electrical stimulation to the adjacent chamber of the heart. The lead 202 is passed through the longitudinal passage of the OTW lead 300 while the OTW lead 300 is fed through the cardiac venous system. As shown in FIG. 4, the OTW lead 300 follows or tracks the lead 202, making the task of guiding the OTW lead 300 substantially easier. Once the distal end 302 and the electrode 308 reach the desired position adjacent the appropriate portion of the heart, the OTW lead 300 may be secured to the lead 202 at the proximal end 304 to preserve the established spacing between the electrode 308 and the helical coil 204. Thus, those skilled in the art will appreciate that the spacing between the electrode 308 and the stent 204 may be varied to account for any variations in the anatomy of the various patients on which it is used.

Figure 2B:
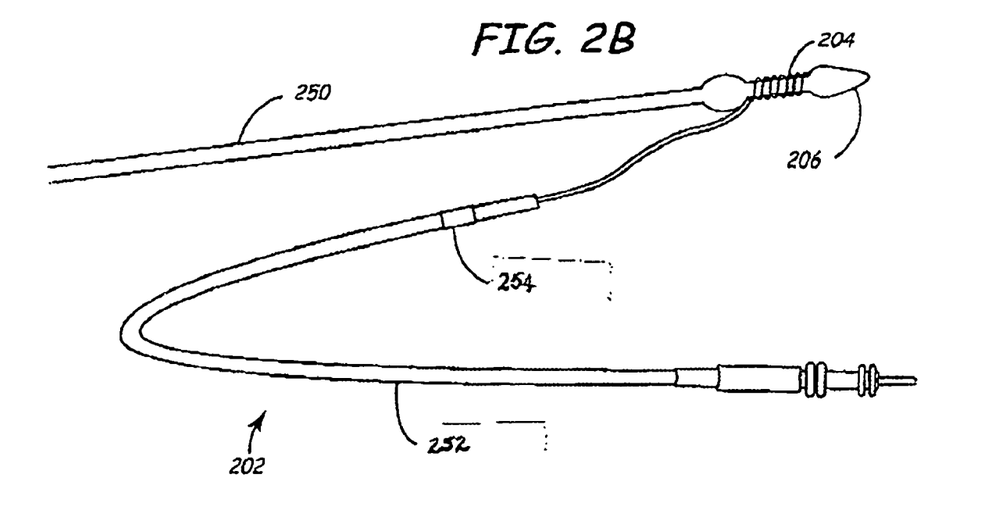
Figure 3B:
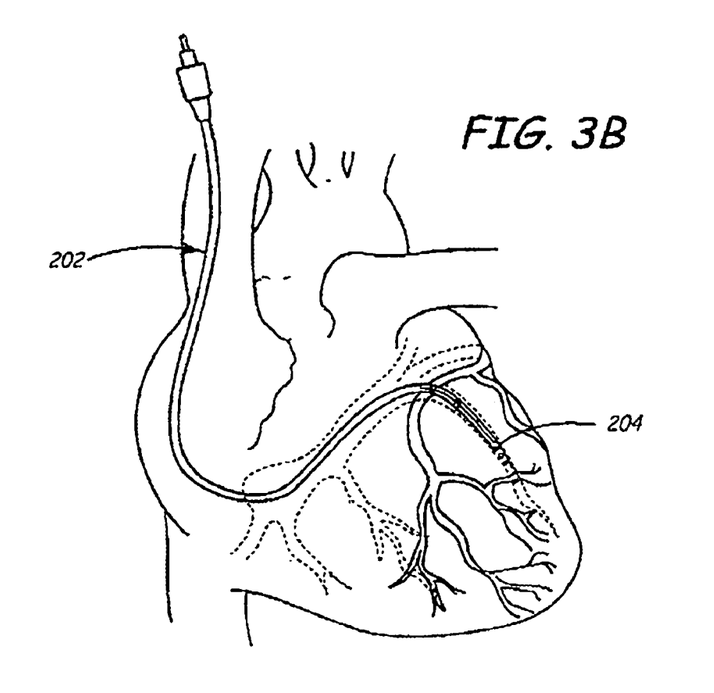

FIGS. 2B and 3B provide a stylized view of a second embodiment of a device, such as a balloon catheter 250, which may be used to pass the lead 202 through the cardiac venous system and then anchor a stent 204 in a desired location in a cardiac vein. In this embodiment, the balloon catheter 250 is an OTW type device that may be guided into the cardiac venous system by a guide wire previously positioned therein by any of a wide variety of well-known techniques. In this embodiment, the lead 202 is formed not only from the fine wire 208 and stent 204, but also includes a second lead 252 coaxially positioned about the fine wire 208 and longitudinally adjustable relative to the stent 204.

In this embodiment, the balloon catheter 250 is guided into the cardiac venous system using the guide wire (not shown) with the entire lead 202 (including the second lead 252) coupled to the balloon 206 via the stent 204. As in the above-described embodiment, once the balloon catheter 250 has reached the desired position with respect to the stent 204 within the cardiac venous system, the balloon may be inflated to urge the stent 204 into substantial contact with the cardiac venous system. In this embodiment, the second lead 252 includes an electrode 352, which may be an anode or a cathode, positioned on its outer surface such that once the lead 202 is in position and the stent 204 has been engaged with the cardiac venous system, the relative positions of the stent 204 and the electrode 352 may be adjusted. As discussed below, this adjustment may be accomplished similarly in both embodiments by sliding the second lead 350 longitudinally along the lead 202.

Figure 5A:
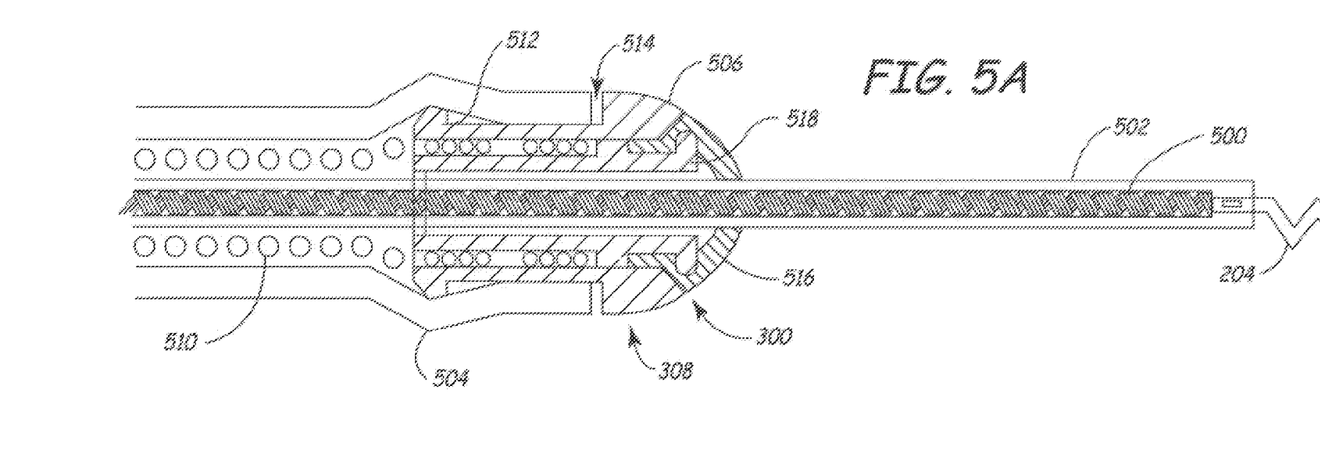
FIG. 5A schematically illustrates a cross sectional view of a first embodiment of a first end portion of the first lead and the over-the-wire lead of FIG. 4.
Figure 5B:
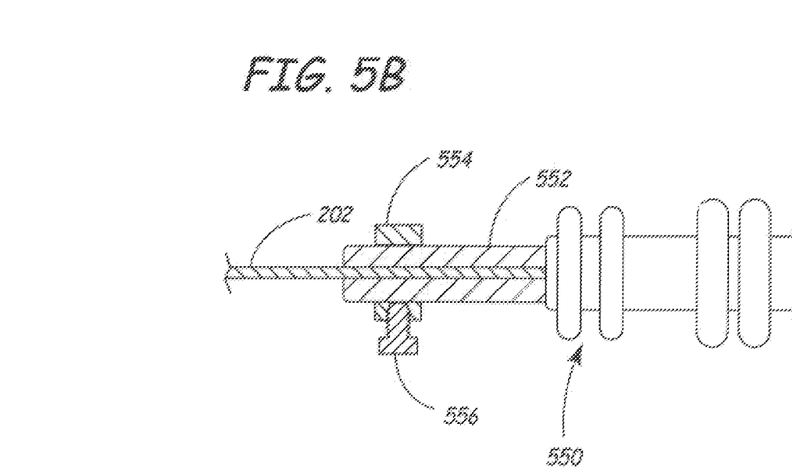
FIG. 5B schematically illustrates a cross sectional view of a first embodiment of a second end portion of the first lead and the over-the-wire lead of FIG. 4.

Turning now to FIGS. 5A and 5B, a cross sectional view of one embodiment of the lead 202 and the OTW lead 300 is shown. The lead 202 is comprised of a flexible conductor 500, such as a metallic wire encased in an insulative material 502, such as polyurethane, silicone, or flouropolymer The helical coil 204 is coupled to the distal end to the flexible conductor 500 such that they are electrically coupled together. Thus, an electrical signal applied to the helical coil 204, such as by a contraction of a chamber of the heart, will pass to the flexible conductor 500, traveling to its proximal end, which may be coupled to the implantable device. Likewise, an electrical signal, such as a pacing signal, applied to the proximal end of the flexible conductor 500 ultimately passes to the helical coil 204, causing the adjacent chamber of the heart to contract. In one embodiment, the lead 202 has an outer diameter of about 0.035 inches.

The OTW lead 300 includes an elongated tubular body 504 that is sufficiently flexible to allow the OTW lead 300 to traverse the tortuous path of the cardiac venous system. In one embodiment, the tubular body 504 is formed from a silicone rubber, polyurethane, or other implantable material, such as a polymer. Further, the tubular body 504 in one embodiment has an outer diameter of about 0.070 inches. The electrode 308 of the OTW lead 300 includes an anode 506 that is formed from a conductive material, such as a platinum alloy or other biocompatible metal, and is located adjacent the distal end portion of the tubular body 504. The anode 506 is generally an open cylinder, having an interior passage 508 generally aligned with the longitudinal passage of the tubular body 504 to allow the lead 202 to pass therethrough. Those skilled in the art will appreciate that the insulative material 502 maintains electrical isolation between the anode 506 and the flexible conductor 500. The anode 506 is electrically coupled to the implantable device by a conductor coil 510 positioned about the interior surface of the tubular body 504. The conductor coil 510, or leads attached thereto, extends along the length of the tubular body 504, reaching the proximal end portion of the OTW lead 300 so that the conductor coil 510 may be coupled to the implantable device. Thus, an electrical signal applied to the anode 506, such as by a contraction of a chamber of the heart, will pass to the conductor coil 510, traveling to its proximal end, which may be coupled to the implantable device. Likewise, an electrical signal, such as a pacing signal, applied to the proximal end of the conductor coil 510 ultimately passes to the anode 506, causing the adjacent chamber of the heart to contract.

The anode 506 is coupled to the tubular body 504 in the illustrated embodiment by a frictional connection and/or adhesive. That is, the outer diameter of the anode 506 is slightly larger than the interior diameter of the tubular body 504. Thus, when the anode 506 is pressed into the flexible tubular body 504, the tubular body 504 expands slightly, tightly gripping the outer surface of the anode 506. An annular lip 512 extends radially outward from the anode 506 so as to further enhance the frictional fit between the anode 506 and the tubular body 504. Further, a recessed region 514 in the anode 506 receives the end portion of the tubular body 504 so that the external diameter of the tubular body 504 is substantially similar to the external diameter of the anode 506. Further, the anode 506 is tapered in a direction extending toward its anticipated direction of travel through the cardiac venous system. The combination of the tapered anode 506 and the similar diameters of the anode 506 and the tubular body 504 presents a relative smooth silhouette that is particularly useful in allowing the OTW lead 300 to pass through the cardiac venous system.

The anode 506 also includes a rubber seal 516 that operates to provide friction between first and second leads to hold relative position and spacing between them while also reducing fluid intrusion (e.g., blood products) into the interior region of the OTW lead 300. Generally, the seal 516 is constructed from a flexible material, such as silicon rubber, and has a central opening sufficient in diameter to receive the lead 202 therethrough. A metal sleeve 518 receives the seal 516 on an end portion thereof and extends into the interior passage of the anode 506. End portions of the seal 516 are captured between the metal sleeve 518 and interior walls of the interior passage within the anode 506 to help secure the seal 516 against removal therefrom.

FIG. 5B shows a cross sectional view of the OTW lead 300 and the lead 202 at their proximal end portions adjacent their connection to the implantable device. In particular, the mechanism for electrically coupling the OTW lead 300 and the lead 202 to the implantable device is shown. A conventional OTW IS-1 connector 550 is coupled to the tubular body 504, extending around the lead 202. In a first embodiment, the insulative material 502 may be stripped away from the lead 202 in a region adjacent a fluted pin portion 552 of the connector 550. Extending about the fluted pin 552 is a collar 554 and setscrew 556 arrangement, which are typically found in an associated pacemaker (not shown). Screwing the set screw into the collar 554 collapses the fluted pin 552 against the now stripped wire 500 of the lead 202 so that substantial electrical contact is made between the fluted pin 552 and the lead 202.

Alternatively, a conventional crimping, piercing tool may be used to puncture the fluted pin 552. The piercing action penetrates the fluted pin 552 and the insulative material 502 of the lead 202, and the crimping action urges a portion of the fluted pin 552 into the opening in the lead 202. Electrical contact between the fluted pin 552 and the electrode is established. Thereafter, the crimping, piercing tool may be removed and an electrical connection between the implantable device and the lead 202 via the OTW connector 550 may be established.

Figures 6A, 6B:
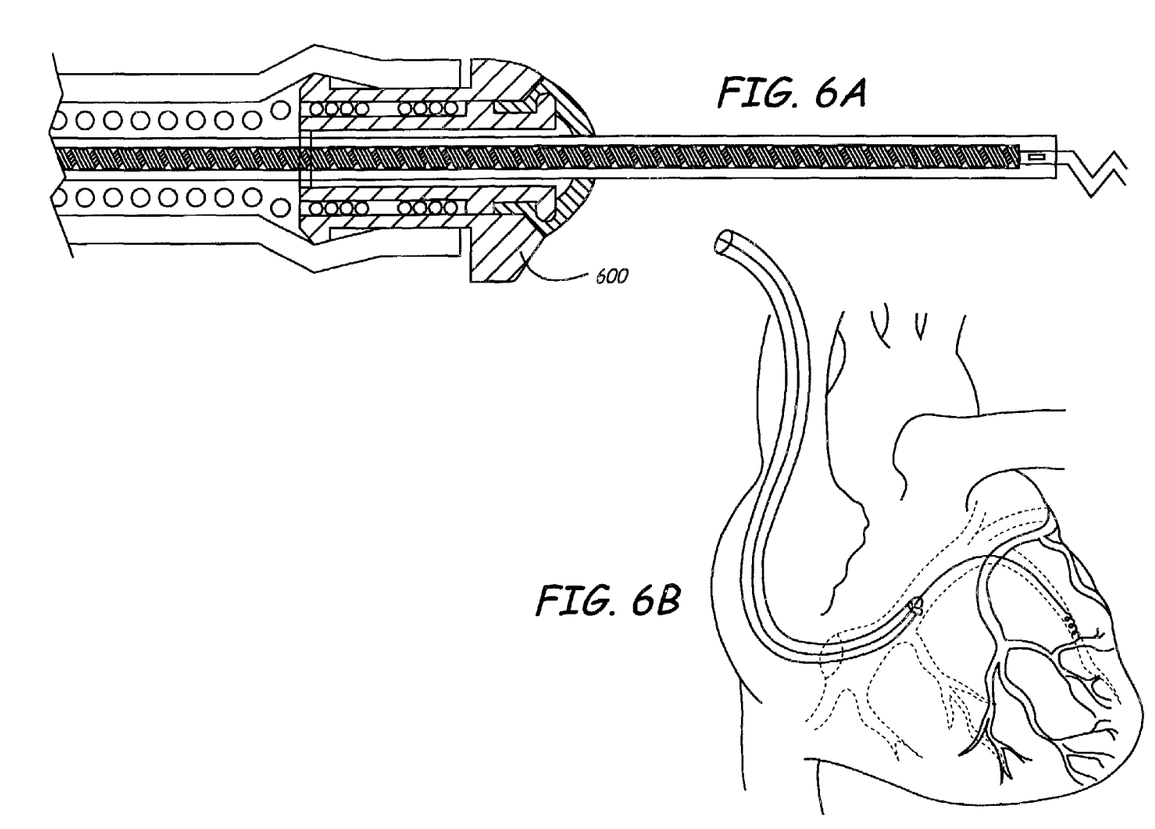
FIG. 6A schematically illustrates a cross sectional view of a second embodiment of the first lead and the over-the-wire lead of FIG. 4.
FIG. 6B schematically illustrates the relative positioning of the leads of FIG. 6A relative to a heart of a patient.

Turning now to FIGS. 6A and 6B, an alternative embodiment of the OTW lead 300 and its desired placement within the body of a patient is illustrated. The illustrated embodiment is intended to provide directional left atrial pacing while also pacing left ventricle. The OTW lead 300 is substantially similar to that shown in FIGS. 5A and 5B with one difference being that the anode 506 includes a directional or eccentric lobe 600 extending radially from the anode 506 over a limited circumferential range. Thus, the directional lobe 600 contacts a sidewall of the vein, spacing it therefrom. The eccentric lobe 600 can be rotated such that good contact is achieve within the coronary sinus. In this embodiment, the OTW lead 300 is spaced further along the cardiac venous system to provide pacing of the left atrium at a slightly different location. Alternatively, pacing can be achieved in both left ventricle and left atrial by stimulating via the cathode at a high voltage which will also stimulating the chamber adjacent the anode.

Figures 7A, 7B:
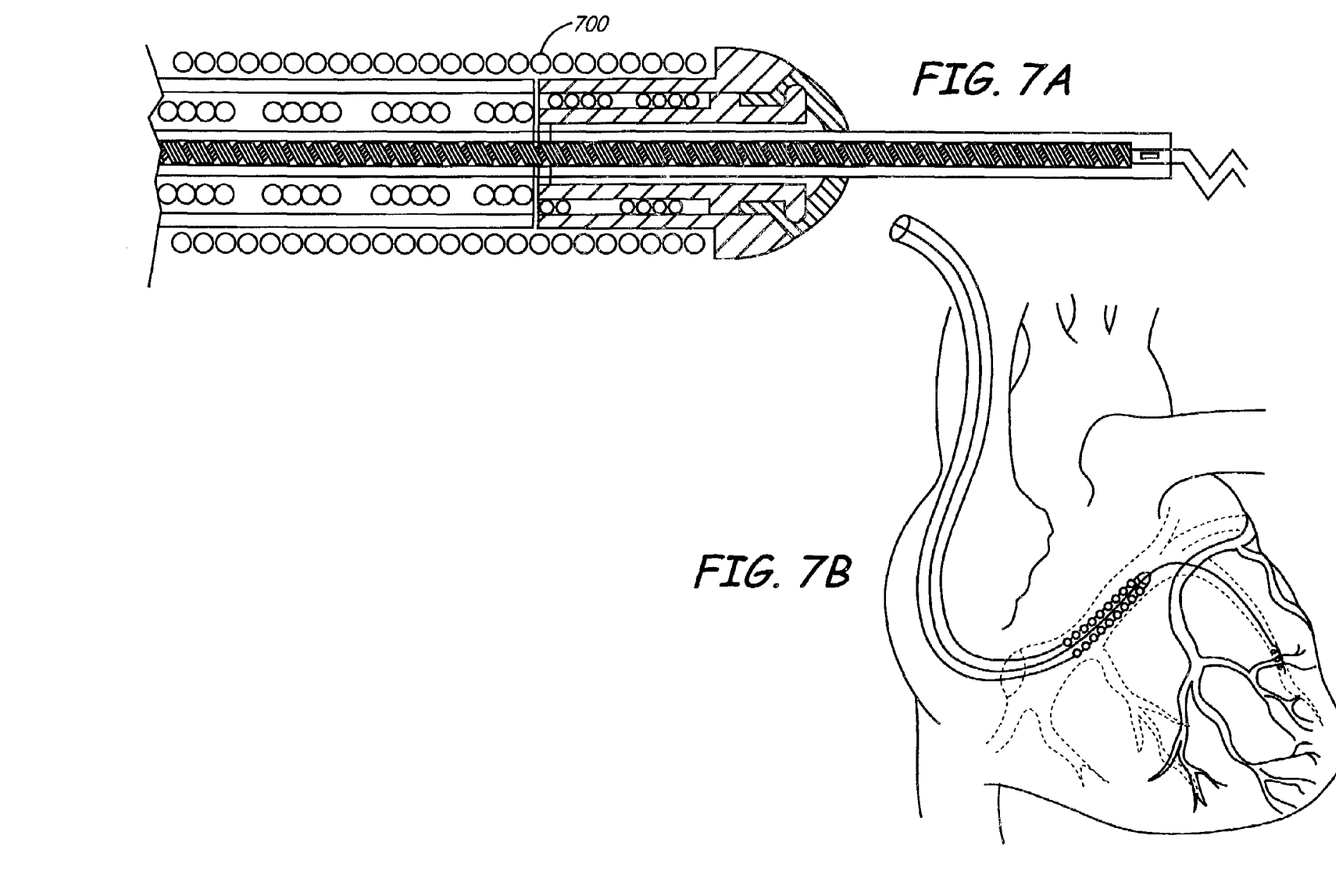
FIG. 7A schematically illustrates a cross sectional view of another embodiment of the first lead and the over-the-wire lead of FIG. 4.
FIG. 7B schematically illustrates the relative positioning of the leads of FIG. 7A relative to a heart of a patient.

Turning now to FIGS. 7A and 7B, an alternative embodiment of the OTW lead 300 and its desired placement within the body of a patient is illustrated. The illustrated embodiment is intended to provide left ventricle pacing with coronary sinus defibrillation. The OTW lead 300 in the embodiment illustrated in FIG. 7A includes a coronary sinus defibrillation coil 700 extending about at least a portion of the outer surface of the tubular body 504 and the anode 506. Further, in the illustrated embodiment, the defibrillation coil 700 provides a mechanism for physically coupling the anode 506 to the tubular body 504. Thus, the annular lip 512 of the embodiments of FIGS. 5A and 6A is not used. The position of the OTW lead 300 in the embodiment described in FIGS. 7A and 7B are substantially similar, ensuring that energy sufficient to defibrillate the heart may be delivered through the anode 506 to a desirable location on the heart adjacent the left atrium. The anode of the OTW lead is adjustable along the first lead to insure good contact with the coronary sinus for defibrillation.

Figures 8A, 8B:
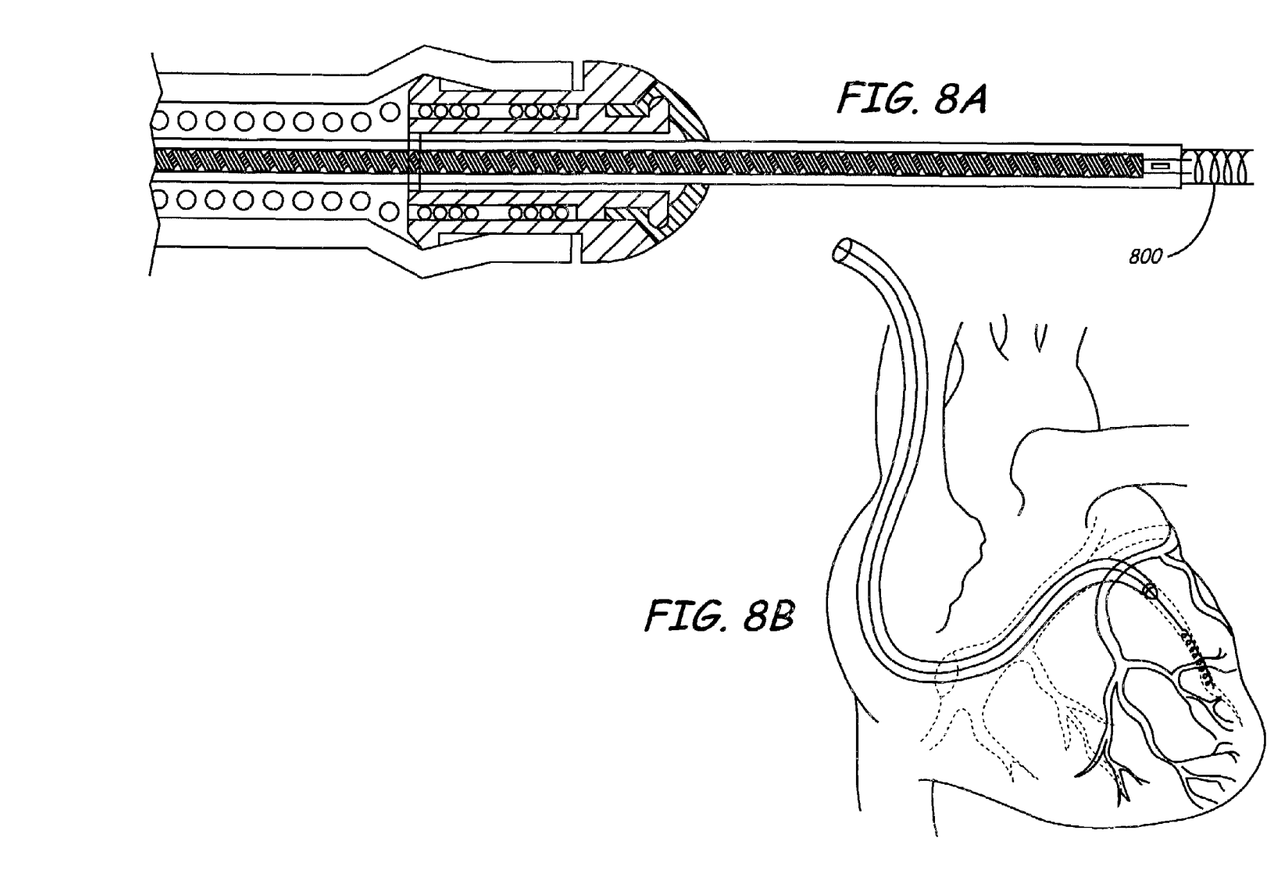
FIG. 8A schematically illustrates a cross sectional view of another embodiment of the first lead and the over-the-wire lead of FIG. 4.
FIG. 8B schematically illustrates the relative positioning of the leads of FIG. 8A relative to a heart of a patient.

Turning now to FIGS. 8A and 8B, an alternative embodiment of the OTW lead 300 and its desired placement within the body of a patient is illustrated. The illustrated embodiment is intended to provide left ventricle pacing with left ventricle defibrillation. The OTW lead 300 is substantially similar to the embodiment shown in FIG. 5A with the exception that the lead 202 is coupled to a defibrillation coil 800. Thus, either pacing signals or a voltage sufficient to defibrillate the heart may be introduced through the lead 202 and the defibrillation coil 800. As shown in FIG. 8B, the OTW lead 300 is positioned further in the cardiac vascular system adjacent the left ventricle.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A medical electrical lead, comprising:
a first implantable lead having a lead body and a first electrode coupled adjacent a distal end portion of the lead body, said distal end portion of said first lead having a fixation device coupled to the lead body and being anchorable in the coronary sinus of a patient; and
a second, over-the-wire implantable lead having a passage adapted to accept the first implantable lead and a second electrode located at the distal end of the passage with a bore, wherein the position of the first and second electrodes may be varied relative to one another by movement of said second lead along said first lead.

2. A medical electrical lead, as set forth in claim 1, wherein said second lead includes an elongated flexible body having first and second end portions and a passage extending therebetween, and wherein said first lead passes through said passage.

3. A medical electrical lead, as set forth in claim 2, wherein the elongated flexible body comprises a flexible tube.

4. A medical electrical lead, as set forth in claim 2, wherein the elongated flexible body comprises a polyurethane tube.

5. A medical electrical lead, as set forth in claim 2, wherein said second lead includes an anode formed of electrically conductive material coupled to a distal end portion of the elongated flexible body, and wherein said anode includes a bore in communication with said passage, and wherein said first lead passes through said bore.

6. A medical electrical lead, as set forth in claim 5, wherein said anode includes a seal coupled thereto and in sliding contact with said first electrode to resist fluid egress into said bore and said passage.

7. A medical electrical lead, as set forth in claim 6 wherein said seal holds said first and second electrodes in relative position during implant.

8. A medical electrical lead, as set forth in claim 5, wherein said anode is tapered along a longitudinal axis of the elongated flexible body and the anode.

9. A medical electrical lead, as set forth in claim 5 wherein the anode further comprises an annular lip and wherein the elongated flexible body extends over the annular lip.

10. A medical electrical lead, as set forth in claim 1, wherein the first and second leads are adapted to be coupled together at their proximal end portions to prevent relative longitudinal movement therebetween.

11. A medical electrical lead as set forth in claim 1, wherein the first and second leads are adapted to electrically couple said first lead to a connector pin of said second lead.

12. A medical electrical lead, as set forth in claim 1, wherein said first lead includes a core of electrically conductive material surrounded by a layer of insulative material.

13. A medical electrical lead, as set forth in claim 12, wherein said first lead includes an electrode coupled to its distal end.

14. A medical electrical lead, as set forth in claim 12, wherein said first lead includes an expandable helical coil coupled to its distal end and a fixed helix for attachment to a heart tissue.

15. A method for positioning a medical electrical lead in a coronary sinus, comprising:
   inserting a first lead within the coronary sinus wherein the first lead includes a first electrode;
   anchoring the first lead within the coronary sinus;
   guiding an over-the-wire lead into the coronary sinus wherein the over-the-wire lead includes a second electrode and the first lead acts as a guide for the over-the-wire lead; and
   adjusting the relative position of the second electrode relative to the first electrode by controlling the position of the over-the-wire lead relative to the first lead.

16. A method, as set forth in claim 15, further comprising fixing the over-the-wire lead against movement relative to the first lead, wherein the position of the first and second electrodes is relatively fixed.

17. A medical electrical lead, comprising:
   a first implantable lead having a lead body and a first electrode positioned adjacent a distal end portion of the lead body and having a fixation device coupled to the end of the lead body;
   a second, over-the-wire implantable lead having a passage adapted to accept the first implanatable lead and a second electrode positioned adjacent a distal end portion thereof; and
   means for adjusting the spacing between the first and second electrodes.

18. A medical electrical lead, comprising:
   a first implantable lead having a lead body and a first electrode coupled adjacent a distal end portion of the lead body, said distal end portion of said first lead having a fixation device coupled to the lead body and being anchorable in the coronary sinus of a patient; and
   a second, over-the-wire implantable lead having a passage adapted to accept the first implantable lead so as to extend coaxially about and be moveable along said first lead, said second lead having a second electrode located thereon wherein the position of the first and second electrodes may be varied relative to one another by movement of said second lead along said first lead.

19. The medical lead of claim 18 wherein said first electrode and said second electrode are implemented as a bipolar pair in left ventricular (LV) pacing.

20. The medical lead of claim 18 wherein said first electrode is implemented for left ventricular (LV) pacing and said second electrode is implemented for left atrium (LA) pacing.

21. The medical lead of claim 18 wherein said first and said second electrodes are implemented as a bipolar pair in left atrium (LA) pacing.

22. The medical lead of claim 18 wherein at least one of said first and said second electrodes is implemented as a defibrillation coil to provide one of LV defibrillation and LA pacing, LA defibrillation and LV pacing, and LV defibrillation and LV pacing.

* * * * *